United States Patent
Ogle et al.

(10) Patent No.: US 7,329,043 B2
(45) Date of Patent: Feb. 12, 2008

(54) THERMAL PROPERTIES TESTING APPARATUS AND METHODS

(75) Inventors: Steven E. Ogle, Murfreesboro, TN (US); Kenneth C. Thompson, Antioch, TN (US); D. Patrick Steagall, Mooresville, NC (US); James Eric DeBord, Nashville, TN (US)

(73) Assignee: L&P Property Management Company, South Gate, CA (US)

( * ) Notice: Subject to any disclaimer, the term of this patent is extended or adjusted under 35 U.S.C. 154(b) by 161 days.

(21) Appl. No.: 10/981,006

(22) Filed: Nov. 4, 2004

(65) Prior Publication Data

US 2005/0117625 A1    Jun. 2, 2005

Related U.S. Application Data

(60) Provisional application No. 60/517,178, filed on Nov. 4, 2003.

(51) Int. Cl.
*G01K 3/00*     (2006.01)
*G01K 7/02*     (2006.01)
*G01N 25/20*    (2006.01)

(52) U.S. Cl. .......................... 374/112; 374/8; 374/43; 374/57; 374/179; 374/166

(58) Field of Classification Search ................. 374/8, 374/112, 166, 179, 43, 57
See application file for complete search history.

(56) References Cited

U.S. PATENT DOCUMENTS

| | | | | |
|---|---|---|---|---|
| 3,545,252 A | * | 12/1970 | Jeter et al. | 374/8 |
| 3,581,552 A | * | 6/1971 | Ringwald et al. | 374/8 |
| 3,667,277 A | * | 6/1972 | Miller et al. | 374/8 |
| 4,229,967 A | * | 10/1980 | Kneifel et al. | 374/8 |
| 6,312,155 B1 | * | 11/2001 | Stool et al. | 374/45 |
| 6,536,943 B1 | * | 3/2003 | Feske | 374/8 |
| 6,991,365 B1 | * | 1/2006 | Pierorazio | 374/8 |

* cited by examiner

*Primary Examiner*—Diego Gutierrez
*Assistant Examiner*—Mirellys Jagan
(74) *Attorney, Agent, or Firm*—Conley Rose, P.C.; Kristin Jordan Harkins

(57) ABSTRACT

An apparatus for testing properties of a product comprising a thermal barrier layer comprises an ignition source, a test stand that extends a sample of the product over the ignition source, and a means for measuring thermal transfer across the sample. The apparatus may further comprise a means for measuring thermal transfer across each layer of the sample. A method for testing properties of a product comprising a thermal barrier layer comprises supporting a sample of the product over an ignition source, heating the sample via the ignition source, and determining a thermal differential across the sample. The method may further comprise determining a thermal differential across each layer of the sample.

20 Claims, 4 Drawing Sheets

THERMAL PROPERTIES TESTING APPARATUS AND METHODS

CROSS-REFERENCE TO RELATED APPLICATIONS

The present application claims the benefit under 35 U.S.C. § 119 of U.S. provisional application Ser. No. 60/517,178 filed Nov. 4, 2003 and entitled "Thermal Properties Testing Apparatus and Methods", hereby incorporated herein by reference for all purposes.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present invention relates to apparatus and methods for testing the thermal properties of a product comprising a thermal barrier layer. More particularly, the present invention relates to apparatus and methods for testing the open flame resistance and thermal transfer resistance of a thermal barrier product comprising a fibrous batt.

BACKGROUND OF THE INVENTION

Thermal barrier products comprising fibrous batts may be used in home furnishings such as couches, mattresses, upholstery, draperies, and the like; protective clothing; building construction; vehicle or airplane seating; insulation; or any other industrial or commercial application for the purpose of fire abatement. In a home furnishings application, for example, a thermal barrier layer comprising a fibrous batt may encase one or more flammable products. Most mattresses and furniture, for example, are filled with polyurethane foam, which is highly flammable. Therefore, a thermal barrier layer may be disposed directly below the ticking provided across the seating surfaces and the borders of a mattress, thereby encasing the subassembly that includes layers of polyurethane foam. Thus, the thermal barrier layer is a fire retardant product that resists burn through due to exposure to an open flame, and also resists thermal transfer to reduce melting and prevent ignition of the more flammable products in the subassembly.

To ensure compliance with state and/or federal flammability standards for industrial and residential furnishings, open flame testing has conventionally been conducted on furniture and bedding as a composite. For example, the state of California has issued Technical Bulletin 603 (TB603), which is a flammability test standard for residential mattresses comprising open flame testing on a foundation and mattress assembly. This approach has inherent drawbacks in that such testing is costly and does not allow for the evaluation of the thermal properties of individual thermal barrier products. Therefore, a need exists for apparatus and methods to test and evaluate the open flame resistance and thermal transfer resistance of thermal barrier products without the cost and complexity of composite open flame testing.

The present invention overcomes the deficiencies of the prior art.

SUMMARY OF THE INVENTION

An apparatus for testing properties of a product comprising a thermal barrier layer comprises an ignition source, a test stand that extends a sample of the product over the ignition source, and a means for measuring thermal transfer across the sample. The test stand may comprise a support plate that supports the sample and a holding plate that holds the sample in place during testing. The apparatus may further comprise an adjustment mechanism for adjusting a displacement between the support plate and the holding plate, and adjustable extensions for leveling the holding plate relative to the support plate. In one embodiment, the holding plate is rotatably moveable with respect to the support plate. The ignition source may comprise a Bunsen burner fueled by a gas. The apparatus may further comprise a shut-off valve for controlling whether gas flows to the ignition source, and a regulator valve for controlling a quantity of gas that flows to the ignition source. In an embodiment, the means for measuring thermal transfer across the sample comprises a thermometer, a first temperature measurement device connected to the thermometer and positioned to measure temperature approximately at the ignition source, and a second temperature measurement device connected to the thermometer and positioned to measure temperature approximately at a surface of the sample furthest from the ignition source. In various embodiments, the first and second temperature measurement devices consist of thermocouples, plate calorimeters, or a combination thereof. The apparatus may further comprise a data collection device, such as a data logger, a computer, or a combination thereof. In an embodiment, the apparatus further comprises means for measuring thermal transfer across each layer of the sample.

A method for testing properties of a product comprising a thermal barrier layer comprises supporting a sample of the product over an ignition source, heating the sample via the ignition source, and determining a thermal differential across the sample. In an embodiment, determining the thermal differential across the sample comprises taking a first temperature measurement approximately at the ignition source, taking a second temperature measurement approximately at a surface of the sample furthest from the ignition source, and calculating the difference between the first and second temperature measurements. The method may further comprise weighing the sample before and after heating to determine the quantity of sample that burned away during testing. In various embodiments, the sample is heated for a predetermined test period, and the thermal differential across the sample is determined a plurality of times on a specified time interval. The properties of a product may consist of open flame resistance, thermal transfer resistance, or both. In an embodiment, the method may further comprise determining a thermal differential across each layer of the sample.

Thus, the embodiments of the apparatus and methods for testing the properties of a product comprising a thermal barrier layer comprise a combination of features and advantages that overcome various problems of the prior art. The various characteristics described above, as well as other features, will be readily apparent to those skilled in the art upon reading the following detailed description of the embodiments of the apparatus and methods for testing a product comprising a thermal barrier layer, and by referring to the accompanying drawings.

BRIEF DESCRIPTION OF THE DRAWINGS

For a more complete understanding of the present invention, and for further details and advantages thereof, reference is now made to the following Brief Description of the Drawings, taken in conjunction with the accompanying drawings, in which.

DETAILED DESCRIPTION OF THE DRAWINGS

Figure 1:
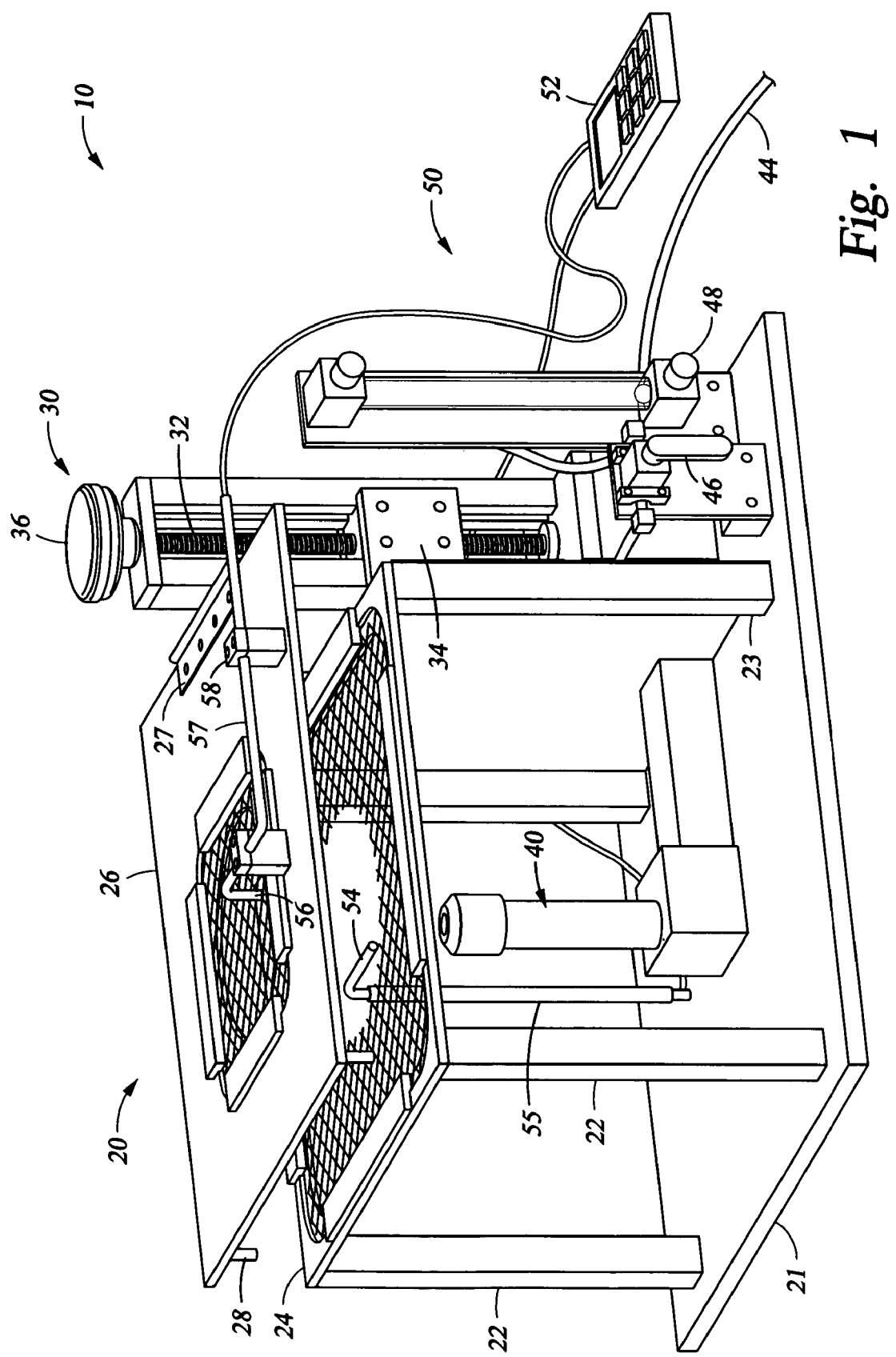
FIG. 1 provides a perspective front view of one embodiment of a testing apparatus for a product comprising a thermal barrier layer.

The apparatus and methods for testing the properties of a product comprising a thermal barrier layer are susceptible to embodiments of different forms. There are shown in the drawings, and herein will be described in detail, specific embodiments of the testing apparatus and methods of testing the properties of the product with the understanding that the present disclosure is for purposes of example only, and is not limiting.

In particular, the apparatus and methods disclosed herein enable evaluation of various properties, such as the open flame resistance and thermal transfer resistance, of an individual thermal barrier product comprising a fibrous batt that may be used in a wide variety of applications, such as, for example, home furnishings such as mattresses, upholstery, draperies, and the like; protective clothing; building construction; vehicle or airplane seating; insulation; or any other industrial or commercial application for the purpose of fire abatement. The testing apparatus and methods disclosed herein may be used for quality control by manufacturers of thermal barrier products, for example, or may be used by purchasers of such thermal barrier products to evaluate their effectiveness.

Further, the testing apparatus and test methods disclosed herein may be used to aid in the selection of various material components for a multi-layered product comprising a thermal barrier layer. One such multi-layered product may comprise a layer of ticking, a layer of thermal barrier product, and one or more layers of foam or other cushioning components, for example. Thus, in the discussion that follows, whenever the testing apparatus and test methods are described with respect to an individual thermal barrier product, one of ordinary skill in the art will readily appreciate that the same apparatus and test methods may also be used to evaluate properties of a multi-layered product comprising a thermal barrier layer.

Figure 2:
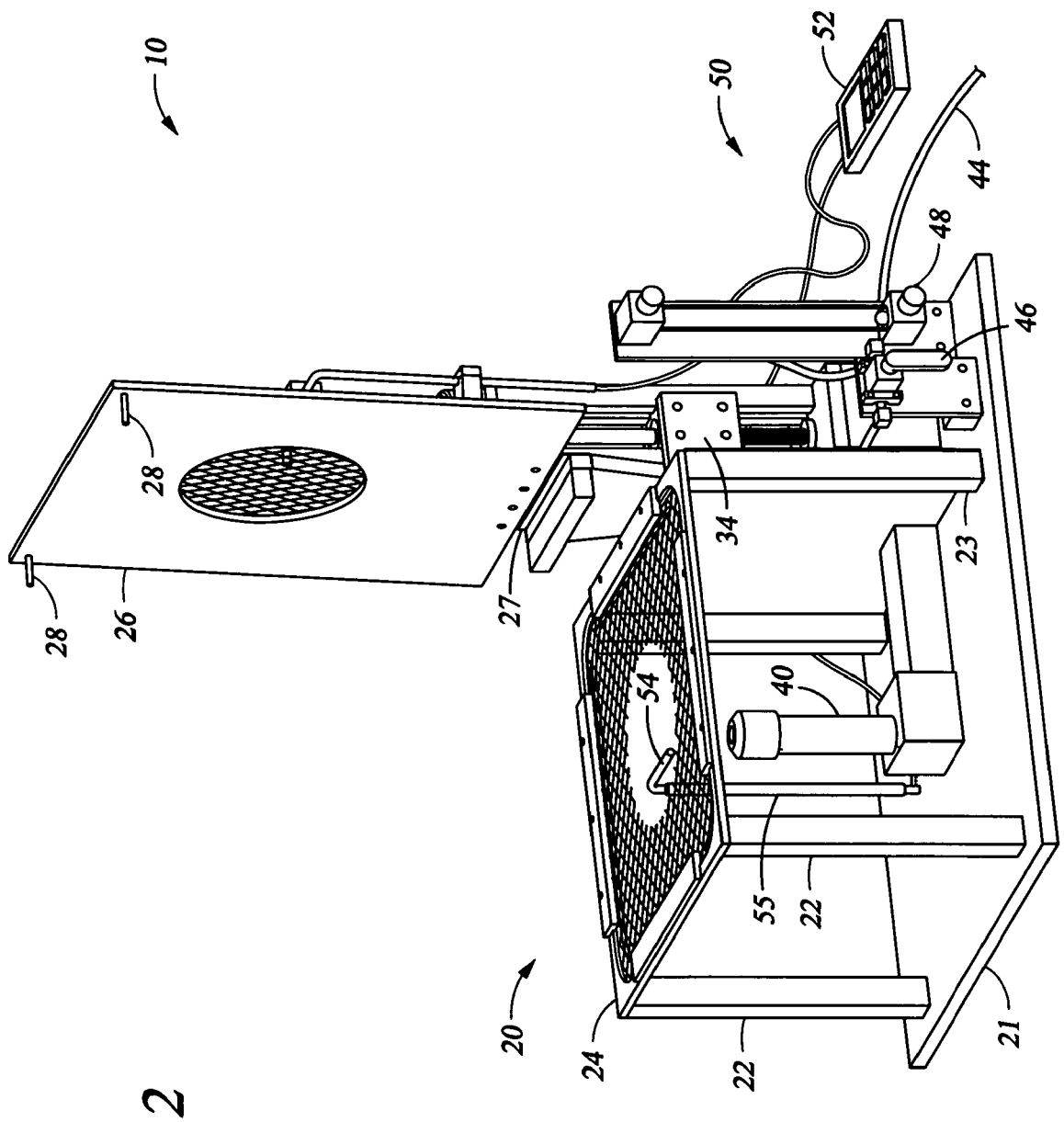
FIG. 2 provides another perspective front view of the apparatus of FIG. 1, showing the holding plate in the raised position.
Figure 3:
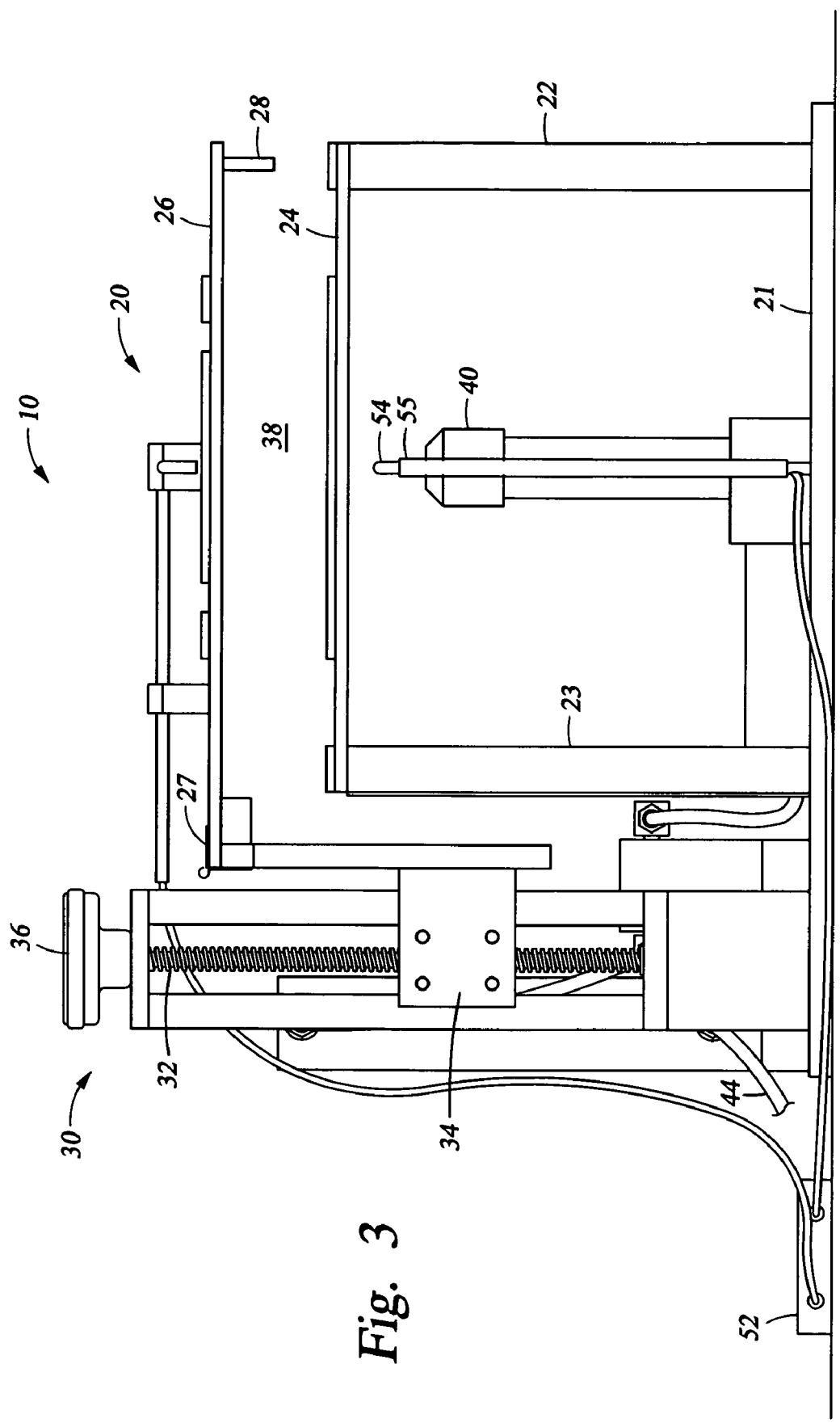
FIG. 3 provides an elevational back view of the apparatus of FIG. 1.
Figure 4:
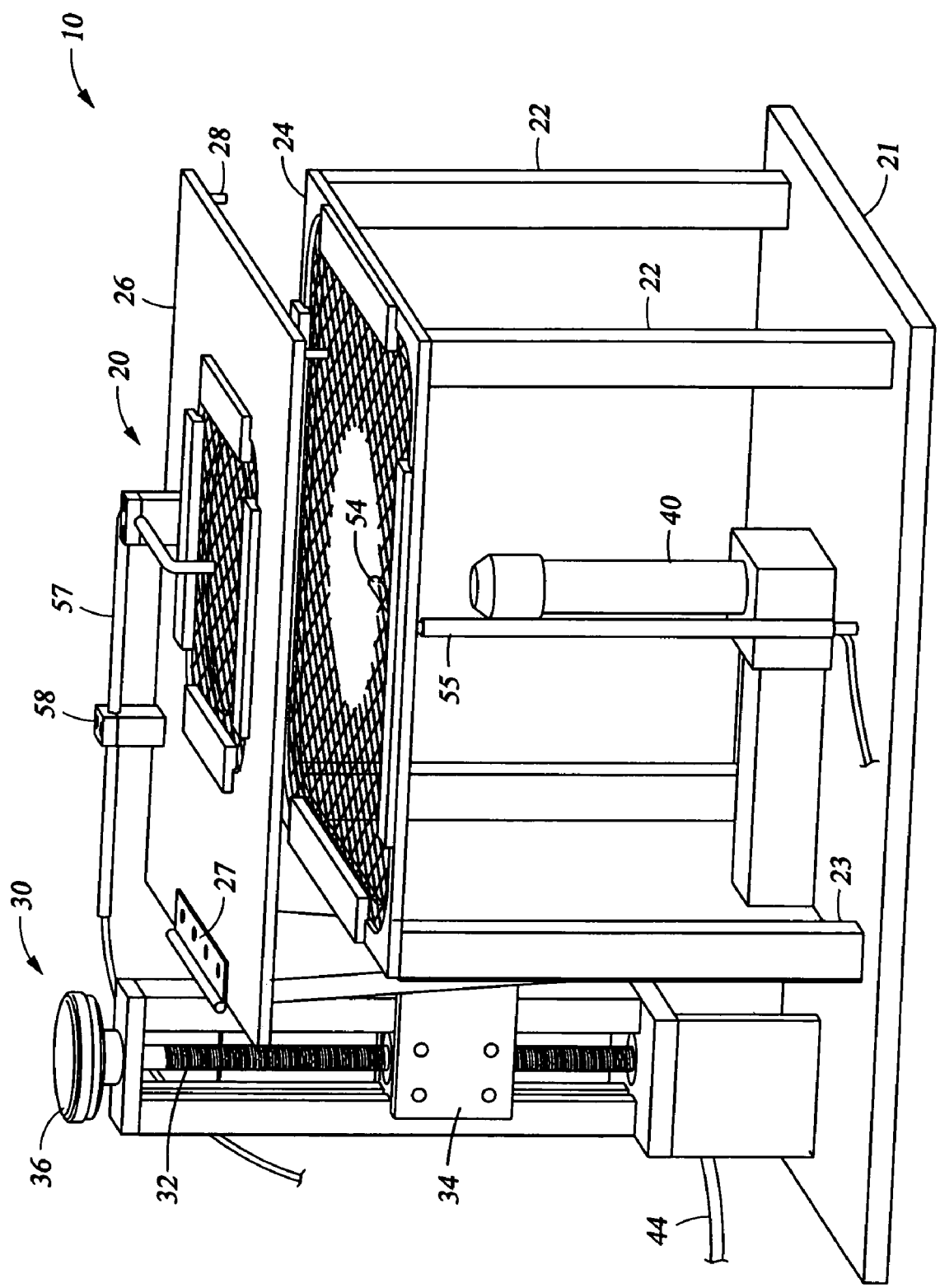
FIG. 4 provides a perspective back view of the apparatus of FIG. 1.

FIG. 1 and FIG. 2 depict a perspective front view of an exemplary testing apparatus 10 in the testing position and in the loading position, respectively. FIG. 3 and FIG. 4 depict an elevational back view of the testing apparatus 10 and a perspective back view of the testing apparatus 10, respectively. As used herein, the term "front" refers to the side of the apparatus 10 that faces the technician during testing, and the term "back" refers to the side of the apparatus 10 opposite the technician during testing.

The testing apparatus 10 comprises a test stand 20, a height adjustment mechanism 30, an ignition source 40, and means 50 for measuring the thermal transfer across a sample of an individual thermal barrier product or a multi-layered product. The test stand 20 comprises an optional base 21, vertical members 22, 23, a support plate 24 for supporting a sample of the product over the ignition source 40, and a holding plate 26 for holding the sample during testing. In an embodiment, the support plate 24 comprises an expanded metal plate with a hole therein to allow flame from the ignition source 40 to heat the bottom surface of the sample, as best depicted in FIG. 2. However, for smaller size samples, the support plate 24 may comprise a solid plate with a hole disposed therein, the hole being sized to allow flame from the ignition source 40 to heat the bottom surface of the sample, while preventing the flame from wrapping around the sides or reaching the top surface of the sample. In an embodiment, the holding plate 26 comprises a thin solid plate having a meshed area therein, and the holding plate 26 may be hinged 27 as depicted in FIG. 2 to be rotatably moveable with respect to the support plate 24, thereby enabling easy loading of the sample to be tested.

As best depicted in FIG. 3, the adjustment mechanism 30 comprises a jack screw 32 connected at 34 to the holding plate 26. A knob 36 is provided at the top of the jack screw 32 to allow height adjustment of the holding plate 26 with respect to the support plate 24, thereby setting the displacement 38 therebetween. The size of the displacement 38 is set according to the thickness of the sample. In an embodiment, the holding plate 26 is provided with adjustable extensions 28 at the end of the plate 26 opposite the adjustment mechanism 30. These extensions 28 allow for the holding plate 26 to be leveled and maintained in a substantially parallel position relative to the support plate 24 at the desired displacement 38. Also, the extensions 28 allow for adjustments of the holding plate 26 position if there are variations in the sample thickness.

Referring again to FIG. 1, the ignition source 40 may comprise a Bunsen burner fueled by a gas, such as propane, for example, supplied via a gas line 44. In one embodiment, the Bunsen burner is a "High-Temperature Bunsen Burner" with 1½ inch grid diameter, available from Cole-Parmer catalog model number U-36130-XX. In an embodiment, the Bunsen burner is capable of producing a 35-kilowatt flame that is 4 to 6-inches in diameter. A shut-off valve 46 and a regulator valve 48 may be operatively connected between the ignition source 40 and the gas line 44. The shut-off valve 46 allows the technician to control whether or not gas flows to the ignition source 40, and the regulator valve 48 allows the technician to control the quantity of gas that flows to the ignition source 40.

The means 50 for measuring the thermal differential across a sample of thermal barrier product comprises a temperature measurement device, such as a digital thermometer 52 operatively connected to a first thermocouple 54 and a second thermocouple 56. In an embodiment, the digital thermometer 52 is capable of reading temperatures in excess of 2000 degrees F. and comprises a dual input thermometer or similar device. A data collection device, such as a data logger and/or a computer, for example, may be connected to the digital thermometer 52 to automatically record temperature readings taken by the thermocouples 54, 56. In an embodiment, the digital thermometer 52 and data logger comprise an "EXTECH EA-15 Thermometer, Data Logger", available from Grainger catalog item number 3WU66, for example.

The first thermocouple 54 takes temperature measurements adjacent the ignition source 40, which represents the temperature at the surface of the sample closest to the ignition source 40, and the second thermocouple 56 takes temperature measurements on the surface of the sample furthest from the burner 40. In an embodiment, the thermocouples 54, 56 comprise type K, Chromel and Alumel thermocouples, such as "Type K High-Temperature Ceramic Fiber-Insulated Thermocouple Probe", available from Cole-Parmer catalog model number 08467-64, for example. In an alternative embodiment, one or both of the thermocouples 54, 56 may be replaced with plate calorimeters, which are capable of making temperature measurements over a wider area, such as 8-inches, for example. Referring now to FIG. 4, in one embodiment the first thermocouple 54 is routed through and held in place by a fixture 55 comprising copper tubing, for example. In another embodiment, the second thermocouple 56 is routed through tubing 57, such as copper tubing, for example, and held in position by a fixture 58.

In another aspect, the present invention relates to a method for testing the properties of an individual thermal barrier layer or a multi-layered product comprising a thermal barrier layer. In one embodiment, an individual thermal barrier layer comprises Pyro~Gon®, an engineered blend of polyester and oxidized polyacrylonitrile (PAN) fibers that may be formed into a unified, flame-resistant fibrous batt by garneting or carding. The PAN fibers are thermal insulating and flame resistant such that when the Pyro~Gon® is subjected to an open flame, the polyester fibers rapidly retreat, leaving a layer of the inert PAN to absorb and disperse the heat.

Sample sections of the thermal barrier product are cut from a finished roll for testing. The first thermocouple 54 is connected to the digital thermometer 52 and positioned adjacent the ignition source 40 so as to extend into the flame. The second thermocouple 56 is connected to the digital thermometer 52 and positioned so as to extend through the holding plate 26 to engage the top surface of the sample furthest from the ignition source 40. As one of ordinary skill in the art will understand, if the test sample comprises a multi-layered product, additional thermocouples may be positioned to engage the top and/or bottom surface of each layer.

The holding plate 26 is then raised as shown in FIG. 2 to load a sample of the thermal barrier product or multi-layered product into the testing apparatus 10. The sample may be placed directly onto the support plate 24, or optionally, a piece of kraft paper may be placed on the support plate 24, with the product sample placed on top of the kraft paper. The holding plate 26 is then lowered as shown in FIG. 1, with the sample being held between the plates 24, 26 for testing. The height adjustment mechanism 30 may be adjusted to change the size of the displacement 38 between the plates 24, 26 according to the sample thickness, and the extensions 28 may be adjusted to level the holding plate 26 as needed.

Once the sample is in place, the shut-off valve 46 is then opened to allow flow through the gas line 44 to light the ignition source 40. The regulator valve 48 may also be adjusted to control the height of the flame from the ignition source 40. The digital thermometer 52 is set to read temperature measurements from both thermocouples 54, 56 while those measurements are recorded at specified time intervals for the duration of the test period. In an embodiment, the specified time interval is 30 seconds, and the duration of the test period is 90 seconds. The technician may manually record these temperature measurements. Alternatively, the temperature measurements may be captured electronically by a data logger or a computer, for example. The temperature differential between the temperature readings taken by thermocouple 54 and thermocouple 56 at each time interval provides a measure of the thermal transfer resistivity of the thermal barrier product. The thermal barrier layer should be effective to prevent ignition of the cushioning layers below it in a mattress subassembly, for example. In one embodiment, the thermal barrier layer is effective in reducing thermal transfer by approximately 70 percent.

The sample is then removed from the testing apparatus 10 and weighed. This weight is compared to the weight of the sample before the burn test to determine the amount of thermal barrier product that was burned away during testing. This evaluation provides a measure of the open flame resistivity of the sample.

Following is a description of one example procedure for testing samples of a thermal barrier product, such as Pyro~Gon®, for example.

EXAMPLE TEST PROCEDURE

The technician obtains a minimum of three cut samples of the thermal barrier product from the production line for testing purposes. Cut samples are taken from a strip, 12 to 16 inches wide cut across the width of the production line or finished roll. The samples are taken from the middle of the floor apron, and from each side of the floor apron. 12-inch by 12-inch samples are prepared by trimming excess material from the cut strip.

The technician weighs each sample and records that weight on a log sheet. If the sample weight falls within specified limits, the technician proceeds to the next step.

The technician measures the loft by placing the sample in a thickness tester under a 1-pound load, or a 5-pound load for densified, needled products. If the sample thickness falls within specified limits, the technician proceeds to the next step.

The technician turns on the gas via the shut-off valve, and adjusts the gas pressure to 20 psig via the regulator valve. The technician then ignites the Bunsen burner, and adjusts the regulator valve so that the floating ball falls between 45 and 55 on the scale, corresponding to about 800 milliliters per minute. At this rate the blue flame should extend no further than ⅛-inch beyond the orifice of the burner. Once the gas flow is set, the technician turns off the gas and proceeds to the next step.

The technician places a type K, ceramic-tipped probe thermocouple in the holding fixture adjacent to the Bunsen burner. The technician ensures that the lead of the thermocouple is connected to the digital thermometer at the T2 terminal. The technician also ensures that the thermocouple is placed between ½-inch and 1-inch away from the orifice of the burner and that it extends approximately ⅛-inch to ¼-inch into the flame.

The technician then connects a type K, ceramic-tipped probe thermocouple to the digital thermometer at the T1 terminal. The technician places a sample onto the support plate and lowers the holding plate onto the sample. The technician ensures that the top thermocouple contacts the surface of the sample by checking for fiber as it is gently raised up. The technician may raise or lower the top thermocouple by adjusting the holding fixture. The technician then removes the sample once all adjustments are made.

The technician turns on the digital thermometer and ensures that readings are being received from both thermocouples, and that the thermocouples are connected to the correct terminals. To verify that the thermocouples are correctly connected, the holding plate may be raised and the burner ignited. In this position, the readings from the top thermocouple should remain approximately at room temperature, while the readings from the lower thermocouple should read the flame temperature, which is normally between 1200 degrees and 1300 degrees F. The technician should ensure that both thermocouples are set to the "K" input on the digital thermometer since a "J" input will produce false readings.

Once the gas flow, flame configuration, and thermocouples are within their specified limits, the technician turns off the gas via the shut-off valve and proceeds to test the samples for thermal properties.

The technician first resets all readings to zero on the digital thermometer by turning the digital thermometer off and turning it on again.

The technician may place a piece of brown kraft paper on the support plate of the test stand, and place the sample on top of the kraft paper. For bi-lofted samples or samples with a sacrificial layer, the sample should be placed with the white polyester or sacrificial layer against the kraft paper. Note: the kraft paper is optional, and it does not affect the outcome of the test. The purpose of the kraft paper is to help keep the sample flat in the test stand, and prevent the sample from bulging through the opening in the support plate.

Once the sample is in place, the technician lowers the holding plate over the sample and verifies that the top thermocouple is making contact with the top of the sample. Then the technician opens the shut-off valve on the gas line and ignites the burner.

The technician presses the "ENTER" button on the digital thermometer and begins recording the time and temperature readings. Specifically, at 30-second intervals, over a 90-second total test period, the technician records the top and bottom thermocouple temperatures in the worksheet provided. Alternatively, a data logger may be set to store the temperature readings electronically.

At the end of the test, the gas is turned off, the holding plate is raised, and the sample is removed. Note: The technician should be wearing leather or heat resistant gloves when lifting the holding plate and removing the sample from the test stand. Also a wet cloth should be on hand, in case the burner overheats causing a flash-back situation. With the gas turned off, the technician may cool the burner by wrapping a wet cloth around it, being careful to avoid steam burns.

The technician repeats these test steps for each of the samples specified in the inspection plan. When all samples have been tested, the technician enters the information collected into the appropriate database or spreadsheet program.

The maximum allowable heat transfer for all Pyro~Gon® products shall be 400 degrees F. The maximum number of failures per production lot shall be no more than 1 failure for every 30 samples tested.

Hourly samples may be drawn from each production lot of material. Samples are taken from a single strip cutting, 14-inches to 16-inches long, across the width of the line, in such a manner that the technician will obtain a minimum of three samples from each cutting representative of the whole line width.

Testing takes place during the day of production. In the case of a failure, the technician identifies which group of rolls the failed strip cutting was obtained from, and an additional sample strip from one roll out of that group is obtained. Should the retest fail, the product is held for further disposition.

While preferred embodiments of the testing apparatus and methods have been shown and described, various modifications and substitutions may be made thereto without departing from the spirit and scope of the invention. Those skilled in the art will readily see other embodiments within the scope of the invention. Accordingly it is to be understood that the example testing apparatus and test methods have been described by way of illustration only and not by way of limitation.

What is claimed is:

1. An apparatus for testing properties of a product comprising a thermal barrier layer, comprising:
    an ignition source;
    a test stand that extends a sample of the product over the ignition source; and
    a means for measuring thermal transfer across the sample;
    wherein the means for measuring thermal transfer across the sample comprises:
        a thermometer;
        a first temperature measurement device connected to the thermometer and positioned to measure temperature approximately at the ignition source; and
        a second temperature measurement device connected to the thermometer and positioned to measure temperature approximately at a surface of the sample furthest from the ignition source.

2. The apparatus of claim 1 wherein the first and second temperature measurement devices consist of: thermocouples, plate calorimeters, or a combination thereof.

3. The apparatus of claim 1 wherein the sample comprises a plurality of layers, and wherein the apparatus further comprises means for measuring thermal transfer across each layer of the sample.

4. The apparatus of claim 1 further comprising a data collection device.

5. The apparatus of claim 4 wherein the data collection device consists of: a data logger, a computer, or a combination thereof.

6. The apparatus of claim 1 wherein the ignition source comprises a Bunsen burner fueled by a gas.

7. The apparatus of claim 6 further comprising a shut-off valve for controlling whether gas flows to the ignition source.

8. The apparatus of claim 6 further comprising a regulator valve for controlling a quantity of gas that flows to the ignition source.

9. The apparatus of claim 1 wherein the test stand comprises a support plate that supports the sample.

10. The apparatus of claim 9 wherein the test stand further comprises a holding plate that holds the sample in place during testing.

11. The apparatus of claim 10 further comprising an adjustment mechanism for adjusting a displacement between the support plate and the holding plate.

12. The apparatus of claim 10 further comprising adjustable extensions for leveling the holding plate relative to the support plate.

13. The apparatus of claim 10 wherein the holding plate is rotatably moveable with respect to the support plate.

14. A method for using the apparatus of claim 1 to test properties of the product, comprising:
    supporting the sample over the ignition source via a support plate on the test stand;
    heating the sample via the ignition source; and
    determining a thermal differential across the sample via the means for measuring thermal transfer across the sample.

15. The method of claim 14 wherein determining the thermal differential across the sample comprises:
    taking a first temperature measurement approximately at the ignition source via the first temperature measurement device connected to the thermometer;

taking a second temperature measurement approximately at the surface of the sample furthest from the ignition source via the second temperature measurement device connected to the thermometer; and calculating the difference between the first and second temperature measurements.

16. The method of claim 14 wherein the sample is heated by the ignition source for a predetermined test period.

17. The method of claim 14 wherein the thermal differential across the sample is determined a plurality of times on a specified time interval.

18. The method of claim 14 further comprising determining a thermal differential across each layer of the sample.

19. The method of claim 14 further comprising weighing the sample before and after heating to determine the quantity of sample that burned away during testing.

20. The method of claim 19 wherein the properties consist of: open flame resistance, thermal transfer resistance, or both.

* * * * *